(12) United States Patent
Nicholson et al.

(10) Patent No.: US 6,241,733 B1
(45) Date of Patent: Jun. 5, 2001

(54) TOME APPARATUS FOR IMPLANTING SPINAL FUSION DEVICE

(75) Inventors: James E. Nicholson, Lincoln; Scott G. Tromanhauser, Marblehead; Dale E. Whipple, East Taunton, all of MA (US)

(73) Assignee: Cortek, Inc., Dedham, MA (US)

( * ) Notice: Subject to any disclaimer, the term of this patent is extended or adjusted under 35 U.S.C. 154(b) by 0 days.

(21) Appl. No.: 09/408,762

(22) Filed: Sep. 30, 1999

Related U.S. Application Data

(62) Division of application No. 09/248,151, filed on Feb. 10, 1999, now Pat. No. 6,096,080.

(51) Int. Cl.[7] .................................................. A61B 17/16
(52) U.S. Cl. ................................................................. 606/84
(58) Field of Search ........................ 606/84, 79; 30/168, 30/167, 167.1; 144/88

(56) References Cited

U.S. PATENT DOCUMENTS

| | | | |
|---|---|---|---|
| 16,041 | * | 11/1856 | Tippett . |
| 113,075 | * | 3/1871 | McConnell . |
| 522,282 | * | 7/1894 | Arthur . |
| 609,366 | * | 8/1898 | Potter . |
| 824,673 | * | 6/1906 | Rockwell . |
| 4,433,681 | * | 2/1984 | Comparetto . |
| 5,571,109 | * | 11/1996 | Bertagnoli ............................. 606/61 |
| 5,722,977 | * | 3/1998 | Wilhelmy ............................. 606/84 |

* cited by examiner

Primary Examiner—Jeffrey A. Smith
(74) Attorney, Agent, or Firm—Williams & Associates; Frederick C. Williams

(57) ABSTRACT

A tome for cutting at least one dovetail in bone is disclosed wherein said tome includes:

a shaft having first and second ends, said first end having attached thereto a blade shaped for cutting the dovetail in the bone and the second end having attached thereto an extension for engagement with mechanical energy transmission devices, and a depth stop on the shaft between the blade and the extension.

21 Claims, 11 Drawing Sheets

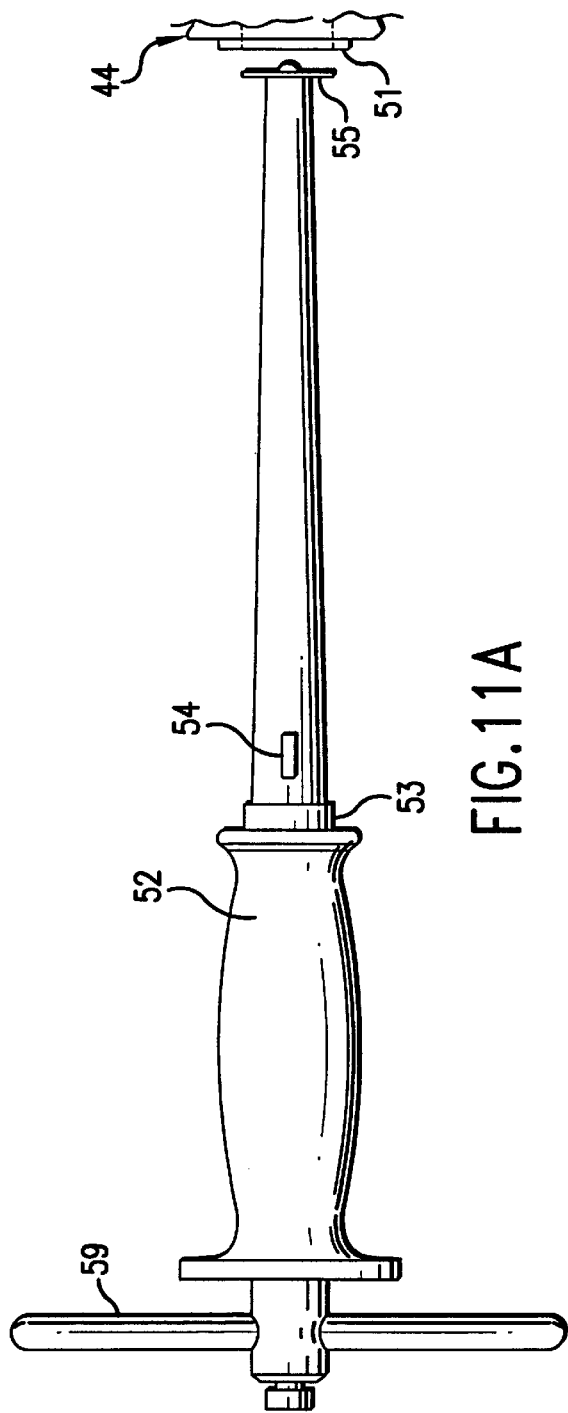
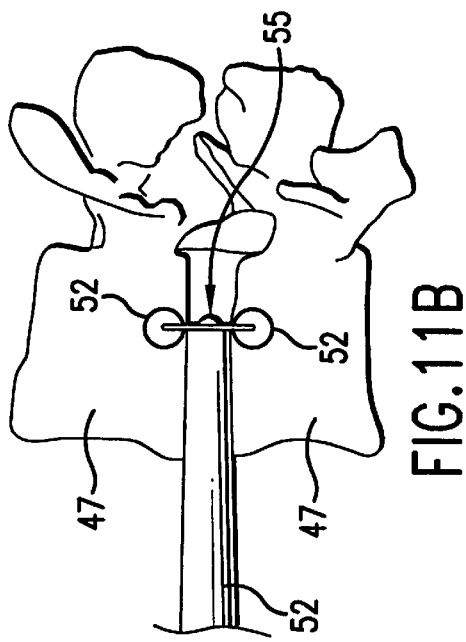
FIG. 11A
FIG. 11B

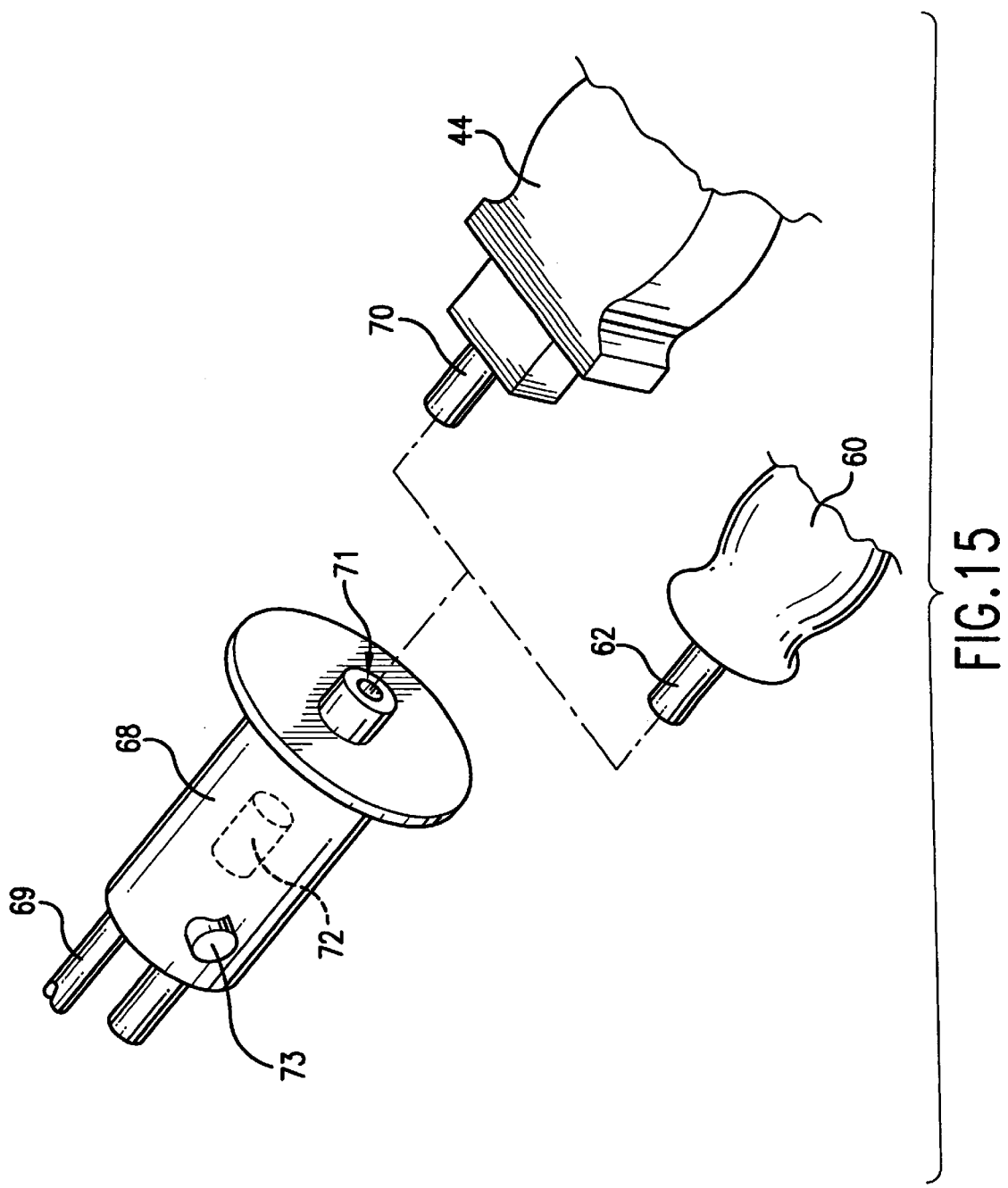

TOME APPARATUS FOR IMPLANTING SPINAL FUSION DEVICE

This application is a division of application Ser. No. 09/248,151 filed Feb. 10, 1999, now U.S. Pat. No. 6,096,080.

BACKGROUND OF INVENTION

Field Of Invention

This invention relates generally to the treatment of injured, degenerated, or diseased tissue in the human spine, for example, intervertebral discs and vertebrae themselves. It further relates to the removal of damaged tissue and to the stabilization of the remaining spine by fusion to one another of at least two vertebrae adjacent or nearly adjacent to the space left by the surgical removal of tissue. More particularly, this invention relates to the implantation of devices which can be inserted to take the structural place of removed discs and vertebrae during healing while simultaneously sharing compressive load to facilitate bony fusion by bone growth between adjacent vertebrae to replace permanently the structural contribution of the removed tissue. This invention further relates to the implantation of devices which do not interfere with the natural lordosis of the spinal column. This invention further relates to implants which are radiolucent to permit more accurate diagnostic imaging follow up.

BACKGROUND OF THE INVENTION

For many years a treatment, often a treatment of last resort, for serious back problems has been spinal fusion surgery. Disc surgery, for example, typically requires removal of a portion or all of an intervertebral disc. Such removal, of course, necessitates replacement of the structural contribution of the removed disc. The most common sites for such surgery, namely those locations where body weight most concentrates its load, are the lumbar discs in the L1-2, L2-3, L3-4, L4-5, and L5-S1 intervertebral spaces. In addition, other injuries and conditions, such as tumor of the spine, may require removal not only of the disc but of all or part of one or more vertebrae, creating an even greater need to replace the structural contribution of the removed tissue. Also, a number of degenerative diseases and other conditions such as scoliosis require correction of the relative orientation of vertebrae by surgery and fusion.

In current day practice, a surgeon will use one or more procedures currently known in the art to fuse remaining adjacent spinal vertebrae together in order to replace the structural contribution of the affected segment of the disc-vertebrae system. In general for spinal fusions a significant portion of the intervertebral disk is removed, and if necessary portions of vertebrae, and a stabilizing element, frequently including bone graft material, is packed in the intervertebral space. In parallel with the bone graft material, typically additional external stabilizing instrumentation and devices are applied, in one method a series of pedicle screws and conformable metal rods. The purpose of these devices, among other things, is to prevent shifting and impingement of the vertebrae on the spinal nerve column. These bone graft implants and pedicle screws and rods, however, often do not provide enough stability to restrict relative motion between the two vertebrae while the bone grows together to fuse the adjacent vertebrae.

Results from conventional methods of attempting spinal fusion have been distinctly mixed. For example, the posterior surgical approach to the spine has often been used in the past for conditions such as scoliosis, using Harrington rods and hooks to align and stabilize the spinal column. In recent years many surgeons have adopted anterior fusion because of the drawbacks of the posterior approach, the primary problem being that in the posterior approach the spine surgeon must navigate past the spinal column and its nerve structure. However, results of anterior surgery are variable and uncertain because constraining the vertebrae from this side does not address the loads put on the spine by hyperextension, such as from rocking the body in a backwards direction.

Pedicle screws and rods, always implanted posteriorly, tend to loosen either in the bone or at the screw-rod interface if fusion is not obtained. Fusion rates for posterolateral instrumented fusions range from 50% to 90%. It must be kept in mind that plain x-rays are only 65–70% accurate in determining fusion status and most studies use this inadequate method to determine fusion status, suggesting that the non-union rate may be greater than reported. It is also known that posterior pedicle screw systems do not prevent all motion anteriorly, leading to the risk of fatigue failure of the metal and screw breakage. This continued motion may also lead to persistent pain, despite solid posterior bony fusion, if the disc was the original pain generator. These well documented failures of pedicle screws have given rise to extensive litigation in the United States.

In contrast to the U.S. common practice of using either IBF devices, implanted from the anterior position, or pedicle screws, implanted posterior, in Europe, spine surgeons use both IBF devices and pedicle screws in combination to achieve stability of the spine. These procedures may be more successful in producing fusion but are far more invasive and costly and have higher morbidity for the patient.

More generally there is a great deal of variability in technique and uncertainty in outcome for the various methods now in use for spinal surgery. For example, Fraser, R. D. points out in "Interbody, Posterior and Combined Fusions," Spine, V20(24S):1675, Dec. 15, 1995, "[A]nalysis of the literature does not indicate that one form of fusion is significantly better than another for degenerative conditions of the lumbar spine." Fraser did not have the results of recent studies involving use of metal interbody cage devices. Ray, Charles D. reported the results of the original IDE study involving his Ray Threaded Fusion Cage (Ray-TFC) in Spine V22(6):667, Mar. 15, 1997. Two hundred eight patients had two year follow-up and were reported to have 96% fusion rate with only 40% excellent results and 25% fair or poor results.

There are only two published reports on the use of the BAK Threaded Interbody Fusion Cage. The first, published by Hacker, R. J., Spine V22(6):660 Mar. 15, 1997 compares posterior lumbar interbody fusion using the BAK device to anterior and posterior fusion with allograft bone. Hacker found that patient satisfaction was equivalent but overall costs were less for the BAK. Zucherman reported on the early experience with laparoscopically assisted ALIF with BAK but no outcomes data are presented on these first 17 patients. Kuslich, S. D. presented the results of the multi-center IDE study of 947 patients who had fusions using the BAK device at the 1996 annual meeting of the North American Spine Society in Vancouver. He reported a fusion rate of 90.5% and some degree of functional improvement in 93% of patients with pain eliminated or reduced in 85.6% of patients. The data so far for these threaded cages is scanty at best. It is clear that the results are better than those for posterior fusion with or without pedicle screw instrumentation but further studies are needed. Problems with threaded devices will no doubt come to light as they are used under less controlled circumstances in greater numbers of patients.

John Kostuick, M.D., Chief of Spine surgery at Johns Hopkins Hospital, Baltimore, Md. (Private Communication with James Nicholson, 2nd R. Roy Camille Meeting, Paris, France, Jan. 28, 1998) vigorously maintains that fusion cannot take place within a metal IBF device which shields the bone from load. Dr. Tromanhauser, one of the inventors, in a series of 30 patients implanted with BAK cages, found that at least 9 patients had continued back pain with x-rays and CT scans that were inconclusive for determining fusion. Surgical exploration of these patients has revealed continued motion and no obvious fusion. All patients were explored at least 6 months after cage implantation, a point at which most surgeons would expect fusion.

Recent unpublished research by Dr. Elsig also indicated that 60% of the cases he reviewed had to be reoperated due to failure 6–8 months after initial surgery. There is therefore recognition and belief, especially among Kostuick Fellows who adhere to the principles of Wolff's law, that loading the bone during fusion through the implant device connecting the opposing remaining vertebrae would yield superior fusion both in strength and in length of healing time.

It is also well established from the study of bone growth that a bone which carries load, especially compressive load, tends to grow and become stronger. Existing stabilizing implants, in particular IBF's, do not share any of the compressive load with the new bone growth, in fact possibly shielding new bone growth from load. For example, the BAK cage is promoted as being so strong that a pair of BAK cages will support the full body load. Such shielding is well known to inhibit new bone growth and healing, however.

The biggest limitation in any method of fusion at the present time is the nature of available devices for bridging the space left by excision of diseased or damaged tissue. In particular, interbody fusion (IBF) devices currently on the market in the United States do not provide stability in all planes of motion. There is very little evidence to support the biomechanical stability of these devices. They are generally stable in compression (forward flexion) unless the bone is osteoporotic, which condition could lead to subsidence of the device into the adjacent vertebral body with loss of disc space height. They may be much less stable in torsion and certainly less so in extension where there is no constraint to motion except by the diseased annulus fibrosus which is kept intact to provide just such constraint. It is doubtful that a degenerative annulus could provide any long term "stiffness" and would most likely exhibit the creep typically expected in such fibrocollagenous structures.

Another problem with conventional fusion devices and with IBF's in particular is difficulty in diagnostic follow-up. In assessing whether or not fusion has taken place between adjacent vertebrae and inside the IBF device, normally plain x-rays including flexion and extension views are obtained. The usual method (Cobb) of measuring motion on these x-rays has a 3 to 5 degree range of error, well beyond the motion that may be present leading to pain. It is impossible to see inside a metal IBF with plain x-rays and conclude anything about fusion status. CT scans with reformatted images are increasingly used because of these shortcomings. Newer software for CT scanners has improved the ability to "see" within cages but the metal artifacts produced by the x-rays are still significant and limit the conclusions that can be drawn. Drs. Tromanhauser and Kant have found virtually no differences in CT scans taken immediately post-op and those taken at a six month follow-up.

Accordingly, there is wide spread recognition among spine surgeons of the need for a flexible radiolucent implant device which would replace removed degenerated tissue and be firmly affixed mechanically to opposing vertebrae. Such a device would dramatically increase the probability of successful fusion because it a) would eliminate or significantly reduce relative movement of the adjacent vertebrae and the intervertebral fixation device in extension and torsion, b) would thereby reduce or eliminate the need for supplemental external fixation, c) by compressive load sharing would stimulate rapid growth of the bone elements packed within the intervertebral device by causing osteoinduction within the bone chips, thereby accelerating fusion, d) would allow confirmation that fusion had taken place using standard CT or possibly plain x-rays, and e) would have the potential to be bioabsorbable, potentially being fabricated from such materials as a D-LPLA polylactide or a remodelable type-two collagen so as to leave in the long term no foreign matter in the intervertebral space. In addition, a flexible implant device can be fabricated in whole or in part from human bone autograft or from bone allograft material which is sterilized and processed, automatically approximately matching the elastic properties of the patient's bone. The success rate of fusion using such an approach is anticipated to exceed the success rate of the IBF devices or the external fusion devices alone and at least equal the combined success rate of the current combination IBF and posterior instrumented technique.

However, there is currently no known method of mechanically affixing an interbody implant device, such as those known in the art as "cages," to adjacent vertebrae. All present IBF devices simply jack open the intervertebral space, relying on the muscle, ligamentous, and annular structures which surround the vertebra to hold the implants in place. The annulus is always degenerative in these cases and could not possibly function in any predictable way and therefore cannot be relied upon to provide adequate motion stability.

Furthermore, prior art cages are filled with bone chips which are shielded from compressive load by the stiff metal cage, preventing natural bone ingrowth through the porous cages because the new bone growth cannot be loaded through the rigid implant. This leads to lack of fusion because the bone, according to Wolff's law, wants to resorb due to stress shielding by the cages. In an effort to overcome this phenomenon, some manufacturers are adding bone growth factors to the cage and/or the bone graft in an attempt to "fool" the bone into fusing through the cage. However, there is no existing method of sharing compressive loads with bone growth material and new bone growth.

Lordosis, which is a pronounced forward curvature of the lumbar spine, is a factor which needs to be taken into account in designing lumbar implants. It is known in the art that preserving the natural curvature of the lumbar spine requires designing into a new device such as the current invention a modest taper approximately equivalent to the effective angularity of the removed tissue. The restoration of normal anatomy is a basic principle of all orthopedic reconstructive surgery.

Therefore there is a perceived need for a device which simultaneously and reliably attaches mechanically to the bony spinal segments on either side of the removed tissue so as to prevent relative motion in extension (tension) of the spinal segments during healing, provides spaces in which bone growth material can be placed to create or enhance fusion, and enables the new bony growth, and, in a gradually increasing manner if possible, shares the spinal compressive load with the bone growth material and the new growth so as to enhance bone growth and calcification. The needed device will in some instances require a modest taper to preserve natural lumbar spinal lordosis. It will also be extremely useful if a new device minimizes interference with or obscuring of x-ray and CT imaging of the fusing process.

Thus it is an object of the current invention to provide a stabilizing device for insertion in spaces created between vertebrae during spinal surgery. It is a further object to create an implantable device for stabilizing the spine by preventing or severely limiting relative motion between the involved vertebrae in tension (extension) and torsion loading during healing. It is a further object to provide a device which promotes growth of bone between vertebrae adjacent to the space left by the excised material by progressive sharing of the compressive load to the bone graft inserted within the device. It is yet a further object to provide mechanical stability between adjacent vertebrae while bone grows through a lumen in the implant and at the same time not diminish the natural lordosis of the lumbar spine. It is a further object of the invention to provide a device which avoids or minimizes interference with various imaging technologies. It is yet another object of this invention to be capable of being fabricated from human bone allograft material.

SUMMARY OF THE INVENTION

The invention disclosed here is a novel implant designed to achieve the foregoing objects. The design of the new implant for spinal surgery includes the possibility of fabricating the device out of material which is elastic, especially in response to compressive loads, preferably with a compressive elasticity closely matched to that of human bone, preferably the patient's bone. In particular, the design includes the capability to fabricate the device from human bone allograft material. The design is also such that the implant mechanically fastens or locks to adjacent vertebrae and stabilizes the involved vertebrae in tension and in torsion while transmitting a portion of the vertical compressive load to new bone growth associated with the device. This feature of the invention will cause osteoinduction within the bone chips loaded into the implant and will share a sufficient portion of the load with existing bone and with the new bone growth to promote further bone growth and not interfere with bone fusion growth. This invention can be tapered to preserve natural lordosis. This invention also minimizes interference with x-ray imaging by virtue of being fabricated in whole or in part from radiolucent materials.

The implant of this invention joins two vertebrae by means of a mechanical fixation device which is hollow to allow bone growth matter to be added to one or more spaces communicating with the top and bottom surfaces for the purpose of promoting fusion. The attachment portion of the mechanical fixation device is, in a first embodiment, a tongue and groove mechanical fastening arrangement. Other mechanical fasteners commonly used in the woodworking art, such as tack and staple devices, can also be used. The mechanical properties of the device are closely matched to the bone's modulus of elasticity so as to promote osteoinduction and rapid bone growth. The devices are generally transparent to existing radiologic imaging techniques so as to allow follow up confirmation of fusion of the adjacent vertebrae. The implant can also be fabricated from bioabsorbable materials so as to leave no long term foreign matter in the body. Human bone allograft material can also be used as the material from which the implant device is fabricated.

In its most general form, the invention is an implant for mechanically attaching to the ends of and promoting bony fusion of at least two vertebrae adjacent to a space left by surgically removed spinal tissue, comprising a load-sharing body comprising a structure having a combination of structural elements fabricated from at least one material having a greater than zero elastic compliance, the combination comprising at least a top surface and a bottom surface; said combination of structural elements establishing for the structure as a whole a composite greater than zero elastic compliance at least in compression in directions generally axial to said top surface and said bottom surface; said combination of structural elements further comprising at least one cavity communicating with both said top surface and said bottom surface in a configuration suitable as a receptacle for bone implant and growth material; and on each of said top surface and said bottom surface at least one fastener capable of mechanically anchoring the body to said adjacent vertebrae and thereby transmitting tensile and torsional loads to and from said adjacent vertebrae.

In another embodiment, the invention generally is an implant for mechanically attaching to the ends of and promoting bony fusion of at least two vertebrae adjacent to a space left by surgically removed spinal tissue, comprising a structure formed from a single piece of bone allograft material and having a top and a bottom, said structure having an internal cavity communicating with said top and said bottom for receiving autograft bone implant material and bone growth factors, said unitary structure having at least one dovetail tongue protrusion on each of said top and said bottom for mechanically interlocking with said adjacent vertebrae by forming a mechanical tongue-and-groove joint.

In yet a third embodiment, the invention is an implant for mechanically attaching to the ends of and promoting bony fusion of at least two vertebrae adjacent to a space left by surgically removed spinal tissue, comprising a composite structure fabricated with at least two separate portions of bone allograft material with different structural properties and having a top and a bottom, said structure having an internal cavity communicating with said top and said bottom for receiving autograft bone implant material and bone growth factors, said unitary structure having at least one dovetail tongue on each of said top and said bottom for mechanically interlocking with said adjacent vertebrae.

An important aspect in the implant procedure is the preparation of the space to receive the implant and the grooves for the dovetail fasteners. A cutting jig is used which distracts the vertebrae and stabilizes them during preparation and acts as a guide for precise cutting. Special tomes are designed to precisely cut the dovetail and prepare the end plate surface. The tomes have an offset which provides for the implant to be sized to slide through the jig but fit very tightly in the space cut into the vertebrae so as to prevent backout of the implant. Once the cutting jig is in place an x-ray is taken to show that the end of the distraction tangs are clearing the spinal canal. The tomes have depth stops which prevent cutting beyond the distraction tangs.

BRIEF DESCRIPTION OF THE DRAWINGS

FIGS. 11A and 11B show further details of a cutting tool or instrument for preparation of the implant site.

FIG. 15 is an isometric view of the driver.

DETAILED DESCRIPTION OF THE PREFERRED EMBODIMENTS

In the currently preferred embodiments, torsional and tensional stability of the spine are provided by fasteners comprising dovetail joints which engage grooves cut during surgery in the vertebrae adjacent to the removed tissue such that the implant and which has large surface contact areas. The dovetails transfer extension and torsional loads between the two vertebrae and the flat contact surface transmits the compressive loads. The device further comprises one or more holes through and/or cavities inside the implant such that the spaces created can be filled with bone graft material which will grow into and attach to the healthy vertebral bone. Optionally in all embodiments tapers to accommodate natural lumbar lordosis can be incorporated as necessary.

In this discussion, we use for convenience a definition of "elastic compliance" as the elastic displacement per unit of applied force, in other words the reciprocal of stiffness. The composite elastic compliance of the device is selected at a value which promotes sharing of compressive load with bone graft and growth material and new bony growth. As discussed at greater length below, in one embodiment, human bone allograft material is used to fabricate the implant. The new fusion bone will gradually share an increasing portion of the compressive loads experienced by the spine because the implant is made of a material, such as a polymer, which has a compressive modulus which works in conjunction with the implant design to closely match the modulus of elasticity of bone during deformation under load. The polymer, or in one embodiment human bone allograft material, has the added advantage of being transparent in x-ray imaging permitting, easy visualization of the fusion process at the vertebral interface. In a variant of one embodiment, metal retaining clips may be located in the implant surface, both above and below the dovetails, to engage the cortical bone and prevent the implant from migrating out of the intervertebral space. The retainers will generally be metal in order to benchmark x-ray imaging for locking engagement assessment. In yet another variation, locking barbs will be included on the implant top and bottom surfaces to assist in securing the implant to adjacent bony surfaces to minimize pullout.

In a second embodiment of the implant, a plurality of dovetail protrusions, or a compound dovetail protrusion in the approximate layout of a horseshoe may be located on the outboard portions of the implant, thereby utilizing the strength and rigidity of the vertebrae to support the spinal column load. In this case the device would contain a hollow central core which would be filled with bone chip and biological medium to accelerate the fusion in the intervertebral space.

Figure 1A:
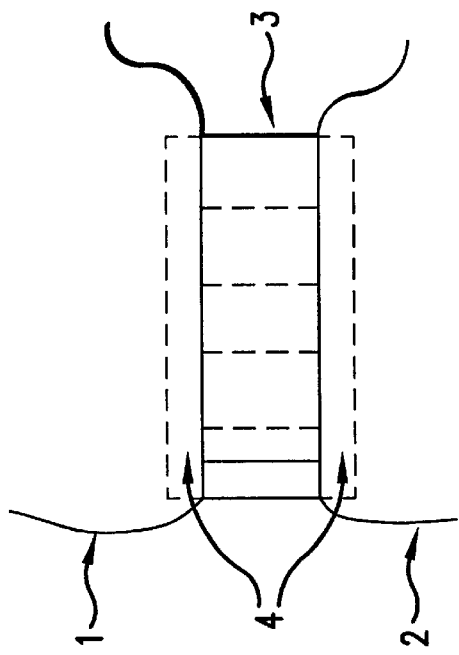
FIG. 1A is a frontal view of an implant of this invention placed between lumbar vertebrae.
Figure 1B:
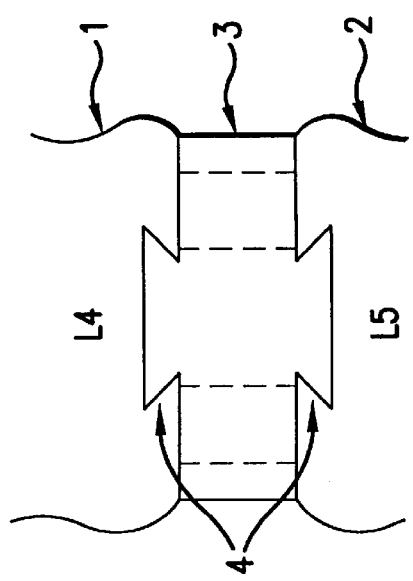
FIG. 1B is a side view of the same implant.
Figure 2:
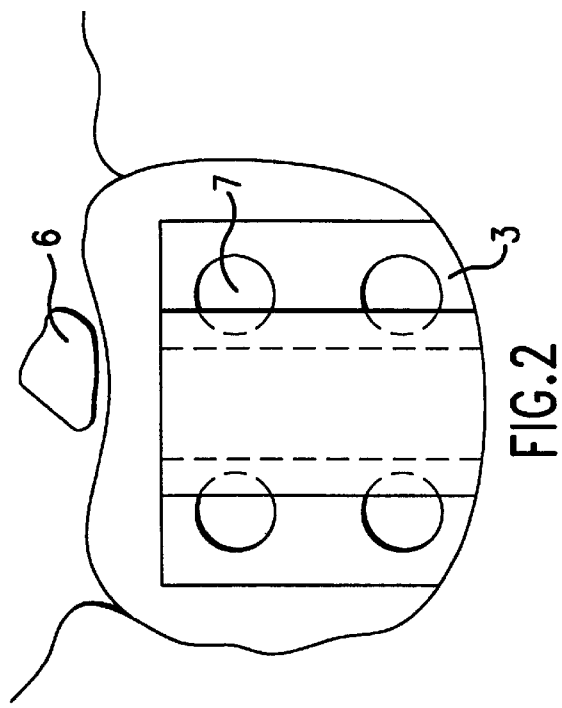
FIG. 2 is a plan view of the same implant.

In the first preferred embodiment, as shown in FIGS. 1A and B (elevation views), vertebrae L4 and L5 (or vertebrae L5 and S1) are mechanically attached by the implant of this invention 3. The device 3 is held mechanically to the adjacent vertebrae 1 and 2 by tongue and groove, or dovetail, arrangements 4. As shown in FIG. 2 (plan view), the implant 3 is sited so as to provide mechanical support to the spine both in compression and in tension, but not so as to intrude into the space 6 occupied by the spinal nerve bundle. In this preferred embodiment, as shown in FIG. 2, the implant 3 will include penetrations or holes 7 the purpose of which is to contain bone growth material to facilitate bony fusion of the adjacent vertebrae. The implant itself may comprise a variety of presently acceptable biocompatible materials such as Polyphenolsulfone, Polyetheretherketone (PEEK), Polysulfone, Acetal (Delrin), UHMW Polyethylene, and composites of these materials involving high strength carbon fibers or REM glass filaments to add tensile and shear strength. As discussed more extensively below, the implant may also be fabricated from human bone allograft material, autograft material, or bone substitute material, such as coral or calcium phosphate. The body of the implant may optionally have a modest taper to accommodate the natural lordosis of the lumbar spine.

One possible problem with an implant with dovetail fasteners fabricated from a material such as polysulfone is that torque on one adjacent vertebra relative to the other may place large tension stresses on the angular portions of the dovetail, thereby causing breaking and crazing of the polysulfone. Thus a variation on this embodiment comprises a composite implant fabricated from plastic material such as polysulfone for the body and titanium for endplates bearing the dovetail protrusions.

Figure 4B:
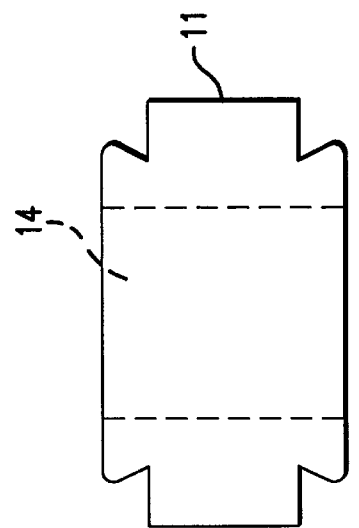
FIG. 4B is a frontal view of a composite implant with inset titanium endplates.
Figure 4A:
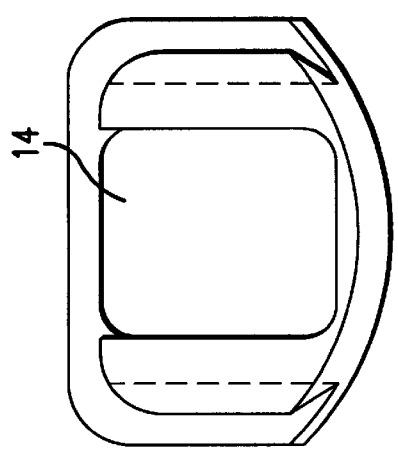
FIG. 4A shows a composite implant with inset titanium endplates in plan view.
Figure 4C:
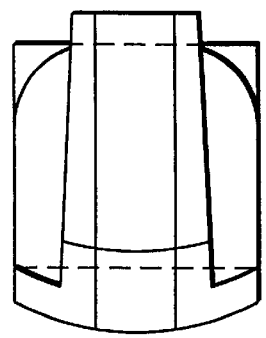
FIG. 4C is a side view of a composite implant with inset titanium endplates.
Figure 3A:
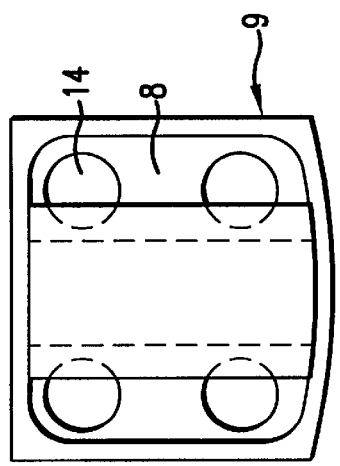
FIG. 3A is a plan view of an implant showing cavities communicating with top and bottom surfaces into which bone growth material is placed.
Figure 3B:
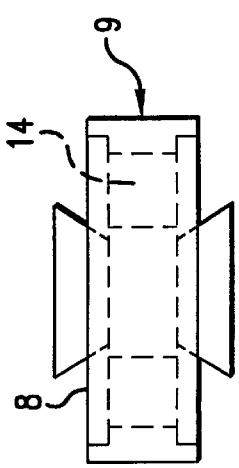
FIG. 3B is a frontal view of the same implant showing cavities.
Figure 3C:
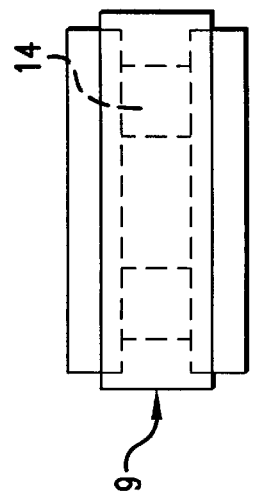
FIG. 3C is a side view of the same implant showing cavities.

FIGS. 3A, 3B, and 3C show one possible arrangement of such a composite structure, with a titanium endplate 8 set into the plastic (and radiolucent) body 9. FIGS. 4A through 4C show a variation on this arrangement with the endplate extending to the shoulders of the plastic body of the implant 11. Both FIGS. 3 and 4 show a variation of this structure, with the titanium endplate 12 set into the plastic body of the implant 9 and 11 in a configuration designed to provide through spaces or cavities 14 in which to place bone growth material. In these latter configurations, the polysulfone body is insert molded into the titanium endplates. The titanium dovetail fasteners possess the tensile strength necessary to avoid fracture or crazing, but the body is still "see through" with respect to X-ray and other methods of visualizing healing progress. In addition, holes in the titanium endplates which are aligned with the bone growth material cavities provides "see through" capability in the vertical direction for assessing new bone growth.

Figure 5:
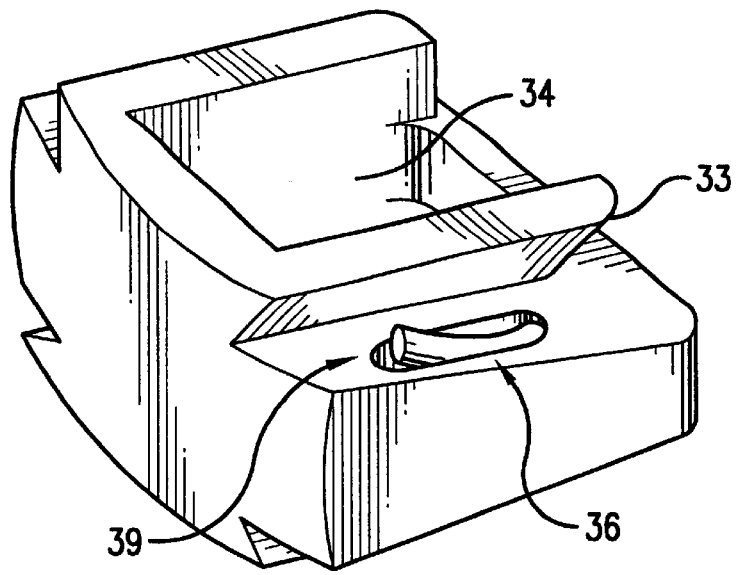
FIG. 5 is an isometric representation of the second embodiment using a horseshoe shaped tongue and groove dovetail fastener and showing the retaining barb.

A second major preferred embodiment, shown in isometric view in FIG. 5, is inserted between two vertebrae, e.g., L4 and L5 or L5 and S1 and mechanically attached by two or more dovetail joints, or by a compound horseshoe shaped dovetail, located on each of the top and bottom surfaces of the implant to the adjacent remaining vertebrae by a composite tongue and groove mechanism similar to but larger than that used to secure the implant of the previous embodiment. In this configuration, the implant comprises either a horseshoe shaped dovetail tongue 33 which in effect creates two dovetail joints per surface toward the outboard ends of the implant top and bottom surfaces or simply two outboard dovetail tongues without the horseshoe top closure. The horseshoe top closure may be substantially curved or it may be substantially straight, with relatively square corners where the dovetail tongue angles back into the body of the vertebra. In a variation on this embodiment, inside the horseshoe shaped dovetail tongue protrusion 33 the body of the implant is hollow, that is, it contains an opening or cavity 34 communicating with both the top surface and the bottom surface into which bone growth material is placed.

Figure 6:
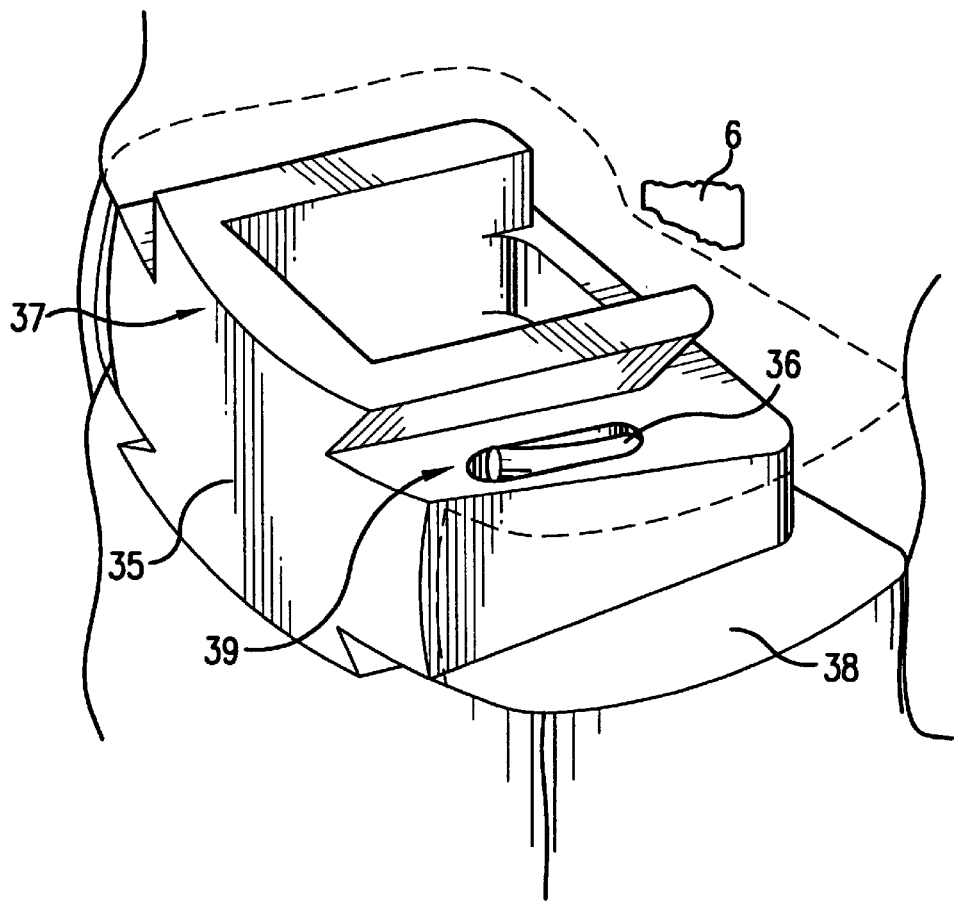
FIG. 6 shows the implant of FIG. 5 inserted between adjacent vertebrae.

In this preferred embodiment, as further shown in the isometric view of FIG. 6, the implant 35 with a relatively squared off horseshoe top closure will have a surface approximately flush with the exterior surface of the adjacent vertebrae and will appear to create one very wide dovetail 37. This embodiment of the implant will also include penetrations or holes in addition to or as an alternative to that shown in FIG. 5, 34, the purpose of which is also to contain bone growth material to facilitate bony fusion of the adjacent vertebrae. As in the prior configuration, the implant 35 is sited so as to provide mechanical support both in compression and in tension to the spinal column, but not so as to intrude into the space 6 occupied by the spinal nerve bundle. The implant in some cases is further inserted inside remaining segments of intervertebral disc tissue 38. As shown in both FIGS. 5 and 6, an optional feature of these embodiments is for the faces of the implant to have locking barbs 36 to retain the implant in place between the remaining vertebrae once it is inserted.

This implant, as in the prior embodiment, may itself comprise a variety of presently acceptable implant materials such as PEEK (Polyetheretherketone), acetal (DELRIN), polysulfone, Ultra High Molecular Weight Polyethylene (UHMW Poly), and composites involving high strength carbon fibers or glass filaments to add tensile and shear strength. Again, as discussed at greater length below, human bone allograft material may be used to fabricate this device. This embodiment may also be fabricated with a modest taper to accommodate natural lordosis.

Figure 7:
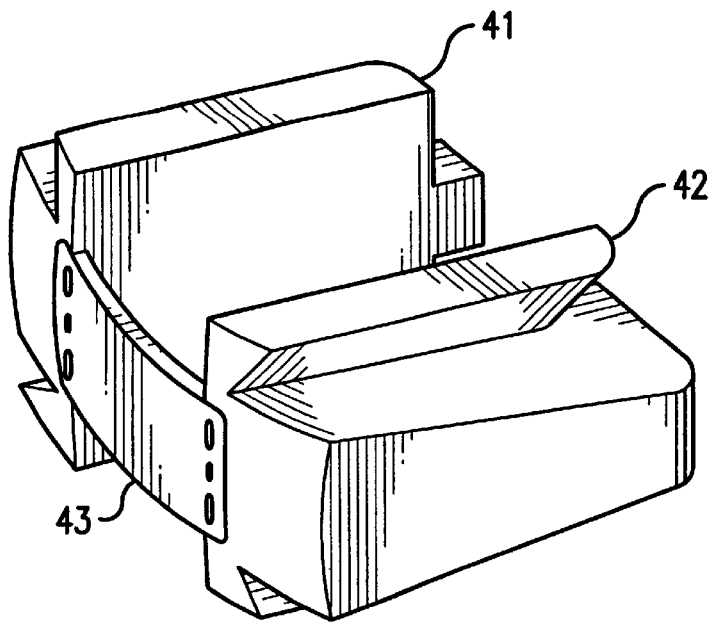
FIG. 7 is an isometric view of a modular implant.

A third preferred embodiment of the lumbar implant, shown in isometric view in FIG. 7, comprises three elements, two modular dovetail halves, 41 and 42, which are inserted between vertebrae L4 and L5 or L5 and S1 and mechanically attached by two dovetail protrusions (similar to those fabricated for the second embodiment) located on the top and bottom of the implant to the adjacent vertebrae by a tongue and groove mechanism similar to but larger than that used to secure previous embodiments of the implant. The two modular dovetail halves are held together by a retainer 43. As in the prior configuration, as shown in the isometric view of FIG. 8, the implant 35 is sited so as to provide mechanical support both in compression and in tension to the spinal column, but not so as to intrude into the space 8 occupied by the spinal nerve bundle.

Figure 8:
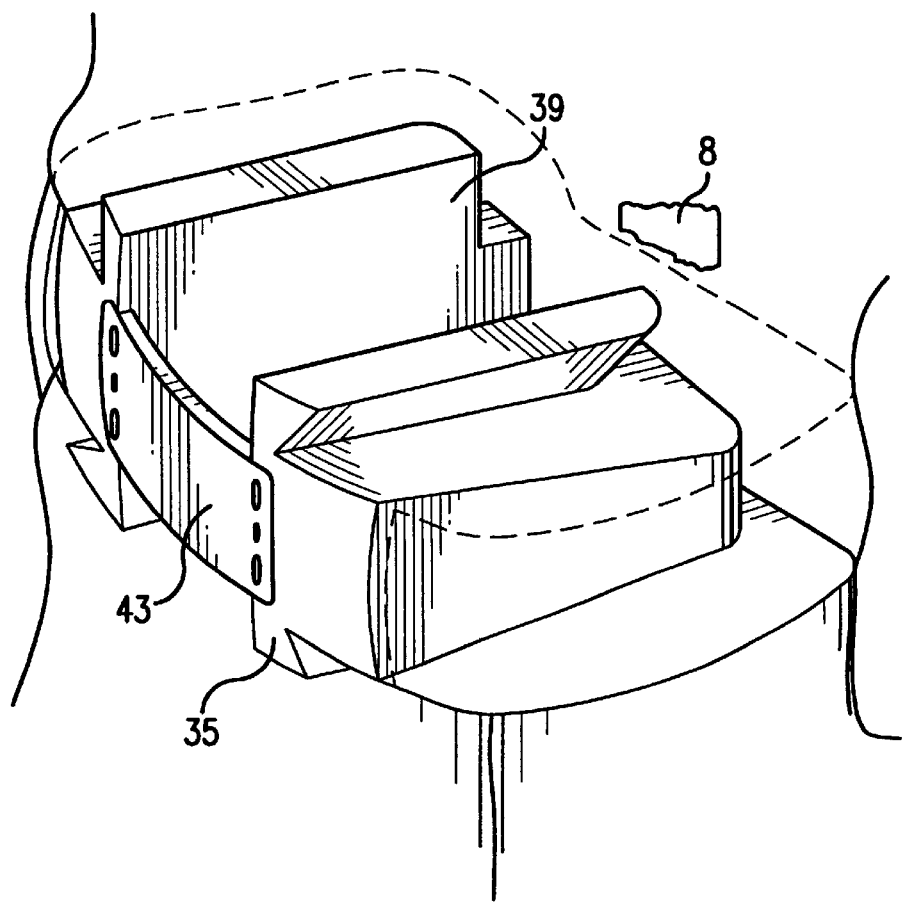
FIG. 8 is an isometric view of the same modular implant with partial depiction of adjacent vertebrae.

In this preferred embodiment, as shown in FIG. 8, the implant 35 will include a cavity 39 the purpose of which is to contain bone growth material to facilitate bony fusion of the adjacent vertebrae. The open space 39 is packed with bone growth material and then capped with a retainer, 43, designed to snap in place to add stability to the implant and to retain the bone growth factor to prevent it from migrating. This implant, as in the prior embodiment, may itself comprise a variety of presently acceptable implant materials such as PEEK (Polyetheretherketone), acetal (DELRIN), polysulfone, Ultra High Molecular Weight polyethylene (UHMW Poly), and composites involving high strength carbon fibers or glass filaments to add tensile and shear strength. Again the modular dovetail halves may be tapered to accommodate lordosis.

Figure 9:
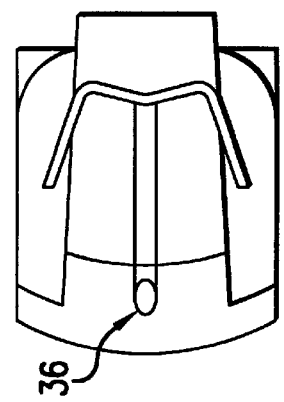
FIG. 9 shows an implant with a retaining barb.

Any of the foregoing embodiments can additionally have a feature shown in FIGS. 5, 6, and 9, namely a retractable barb 36. This barb comprises a spring wire which when deployed engages the adjacent vertebrae to prevent the implant from dislodging. A retraction tool may be inserted into the hole 39 to cause the sigma-shaped barb to retract its probe-like end so that the implant disengages from the adjacent vertebra.

As previously noted, any of the foregoing embodiments of the Cor-Lok™ interlocking implant can be fabricated from cadaver bone which is processed to form bone allograft material. Tissue grafting of living tissue from the same patient, including bone grafting, is well known. Tissue such as bone is removed from one part of a body (the donor site) and inserted into tissue in another (the host site) part of the same (or another) body. With respect to living bone tissue, it has been desirable in the past to be able to remove a piece of living tissue graft material which is the exact size and shape needed for the host site where it will be implanted, but it has proved very difficult to achieve this goal.

On the other hand, processing of bone material which does not contain living tissue is becoming more and more important. Non-living bone grafting techniques have been attempted both for autografts and for allografts. For example, Nashef U.S. Pat. No. 4,678,470 discloses a method of creating bone graft material by machining a block of bone to a particular shape or by pulverizing and milling it. The graft material is then tanned with glutaraldehyde to sterilize it. This process can produce bone plugs of a desired shape.

In the Nashef process, the process of pulverizing or milling the bone material destroys the structure of the bone tissue. The step of tanning it with glutaraldehyde then renders the graft material completely sterile.

In the prior art, inventors have believed that it is desirable to maintain graft tissue in a living state during the grafting process. There is no doubt that the use of living tissue in a graft will promote bone healing, but much surgical experience has shown that healing can be achieved with allografts o of non-living bone material which has been processed. In fact, spine surgeons express a distinct preference for such materials, and at least one supplier, the Musculoskeletal Transplant Foundation (MTF), has introduced femoral ring allografts for spine surgeries.

It is now possible to obtain allograft bone which has been processed to remove all living material which could present a tissue rejection problem or an infection problem. Such processed material retains much of the structural quality of the original living bone, rendering it osteoinductive. Moreover, it can be shaped according to known and new methods to attain enhanced structural behavior.

Research shows that such allografts are very favorable for spinal surgery. According to Brantigan, J. W., Cunningham, B. W., Warden, K., McAfee, P. C., and Steffee, A. D., "Compression Strength Of Donor Bone For Posterior Lumbar Interbody Fusion," Spine, Vol. 18, No. 9, pp. 12113–21 (July 1993):

Many authors have viewed donor bone as the equivalent of autologous bone. Nasca et al. . . . compared spinal fusions in 62 patients with autologous bone and 90 patients with cryopreserved bone and found successful arthrodesis in 87% of autologous and 86.6% of allograft patients.
(Citations omitted.) Moreover, as previously noted, sources of safely processed allograft material have recently become available.

In the present invention, allograft bone is reshaped into one of the Cor-Lok™ configurations for use as a spine implant. Various methods, including that of Bonutti, U.S. Pat. Nos. 5,662,710 and 5,545,222, can be used to shape the allograft material into the desired shape.

In the first sub-embodiment of this aspect of the current invention, bone material which yields to compressive loads at the exterior surfaces without significant degradation of the interior structural properties, such as cancellous or trabecular bone, is shaped. It is not unusual that reshaping of graft tissue is necessary to obtain the best possible graft. In particular, bone tissue may be stronger and better able to bear force when it is denser and more compact.

Compression of allograft bone is desirable from general considerations. Generally, bone samples are stronger when they are more dense. Compressing allograft bone increases its density and thus generally strengthens the allograft. The allograft bone also stays together better. In addition, recent studies have indicated that the shell of vertebral bone is very much like condensed trabecular bone. Mosekilde, L., "Vertebral structure and strength in vivo and in vitro," Calc. Tissue Int. 1993;53(Suppl):121–6; Silva, M. J., Wang, C., Keaveny, T. M., and Hayes, W. C., "Direct and computed tomography thickness measurements of the human lumbar vertebral shell and endplate," Bone 1994;15:409–14; Vesterby, A., Mosekilde, L., Gunderson, H. J. G., et al., "Biologically meaningful determinants of the in vitro strength of lumbar vertebrae," Bone 1991;12:219–24. Compressing bone allograft material prior to implantation thus generally produces a stronger graft.

Compression also allows conversion of larger irregular shapes into the desirable smaller shape, thereby permitting more disparate sources of allograft bone to be used. By compressing bone to a given shape it is possible to configure the allograft to match a preformed donee site prepared by using a shaped cutter to cut a precisely matching cut space. In particular, this method of formation facilitates the formation of dovetail tongue protrusions on the upper and lower surfaces of the implant for the formation of a tongue-and-groove mechanical joint with adjacent vertebrae.

In the current invention, a blank is cut from cancellous or trabecular allograft bone and placed in a forming apparatus. The forming apparatus compresses the sample into the desired shape. In particular, this process forms the dovetail tongue protrusions on the implant upper and lower surfaces for the tongue-and-groove joint. The cancellous or trabecular material yields at the external surface under the pressure to form a compacted layer around the outside of the allograft form. This compacted layer is not destroyed material but rather forms substantially a structure with properties of the vertebral shell or of a monococque design, including additional structural properties such as enhanced tensile strength. This enhanced tensile strength enables the allograft material to perform the same function in resisting torsion and extension of the spine as does the synthetic materials previously discussed. Such processes in general are able to maintain the homologous property of the allograft material.

In the second embodiment of this aspect of the current invention, different types of allograft bone are formed into a composite structure to provide the necessary structural properties. Both cortical or shell and dense cancellous or trabecular bone may be compacted into a unified structure. Fibrin "glue" is highly suitable for use as an adhesive in such structures. Fibrin is a blood component important in blood clotting. It can be separated or centrifuged from blood and has the nature of an adhesive gel. Fibrin can be used as an adhesive, either in a natural state or after being compressed, to hold together material such as separate tissue pieces pressed together in a tissue press. In particular, cortical bone from the same source can be used as a shell to provide needed additional structural properties, such as tensile strength to a composite shape. Cortical bone can also be provided in a shell, much like the known femoral ring implants, to provide the needed structural properties. Moreover, a shell is not the only structural element which can be added in this way. Buttresses, gussets, cross-braces, and other structural elements can be included in the same way. Using such materials, the homologous property of the bone allograft material may be maintained.

In another sub-embodiment, a relatively thin external shell of a synthetic material can be provided for enclosing compressed allograft material and providing any needed additional structual properties. After the graft is compressed, the shell is placed around the graft. The shell may be made of a material which expands after it is placed in the spine, thereby supplementing the interlocking properties of the Cor-Lok™ mechanical design by improving the fill between the allograft and the donee site. There are a number of suitable materials which expand when they come in contact with water or other fluids. One is PEEK (polyetheretherketone)(water absorption about 1.5%). A desiccated biodegradable material or suitable desiccated allograft material may also be used.

The expansion can take place in one of two ways. First, the retainer can itself be compressed, as with the tissue, then expand when placed in the body. Second, the retainer can be made of a material which expands when it comes in contact with water or other bodily fluids.

It should be noted that the entire allograft implant can itself be compressed so that it expands when contacted by water. The expandable shell material can first be compressed with the allograft material, which then expands when placed in the body.

It should further be understood that the graft can be multiple tissue fragments rather than a composite material. The compressing process can be used to compress multiple bone fragments into one larger piece. It should also be understood that the compression process can be used to add additional materials to an allograft composite. For example, to bone tissue there can be added tri-calcium phosphate, an antibiotic, hydroxyapatite, autografts, or polymeric materials.

FIGS. 10A through 16B depict the surgical tools used to install the implant. This apparatus comprises a set of unique tools which will accurately cut a dovetail joint in bone for the purpose of inserting an implant which locks adjacent vertebrae together.

Figure 10A:
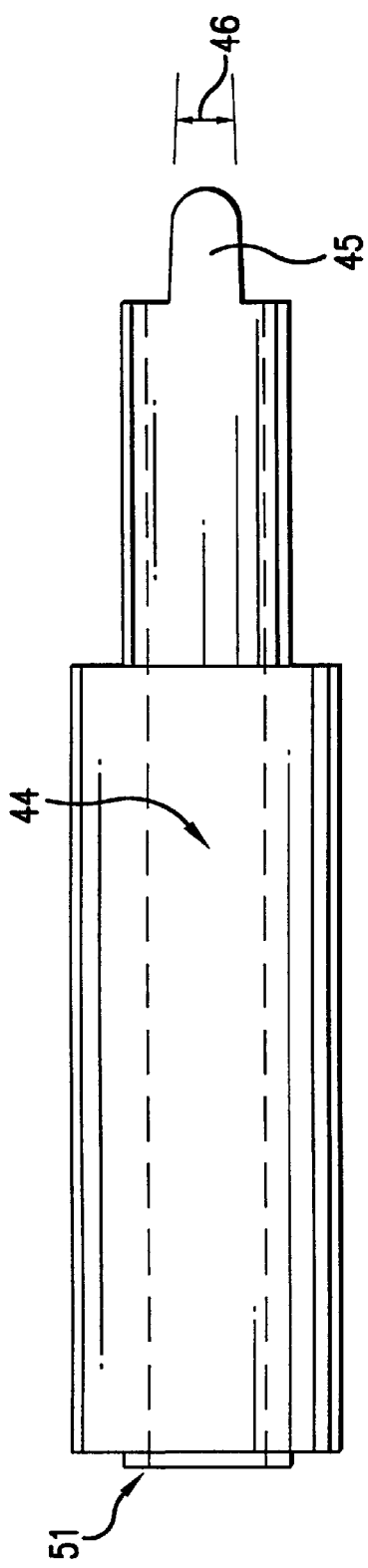
FIGS. 10A and 10B depict the handle of the emplacement instruments for preparation of the implant site.
Figure 10B:
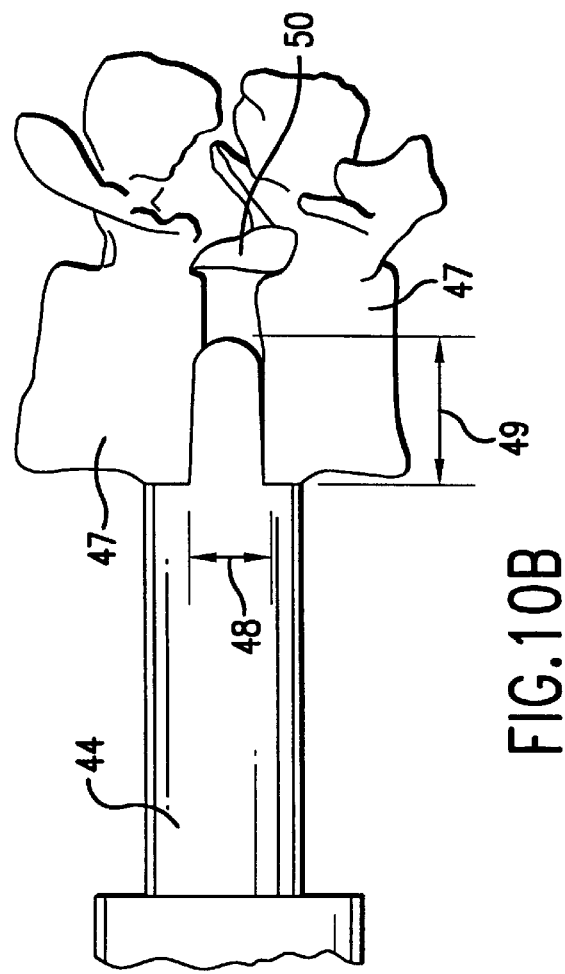

The guide 44, shown in FIGS. 10A and 10B, is a tubular tool with tangs 45 extending from one end. The tangs, tapered 46 to conform to natural lordosis, are inserted between the vertebrae 47 and distract them to a preferred dimension 48, as shown in FIG. 10B. The driver 68, shown in FIG. 15, can be used with a rod extension guide adapter 70, also shown in FIG. 15, to drive the guide 44 into place. This step establishes a fixed reference relative to the two vertebrae 47 and secures the vertebrae from moving. The length 49 of the tangs 45 is consistent with the other tools in the set and establishes the extent 49 to which any tool can penetrate. A lateral x-ray is used to assure that the extent of penetration 49 is safely away from the spinal canal 50. All of the other tools have positive stops which contact the guide depth stop 51 to control the depth of cut.

Figure 12B:
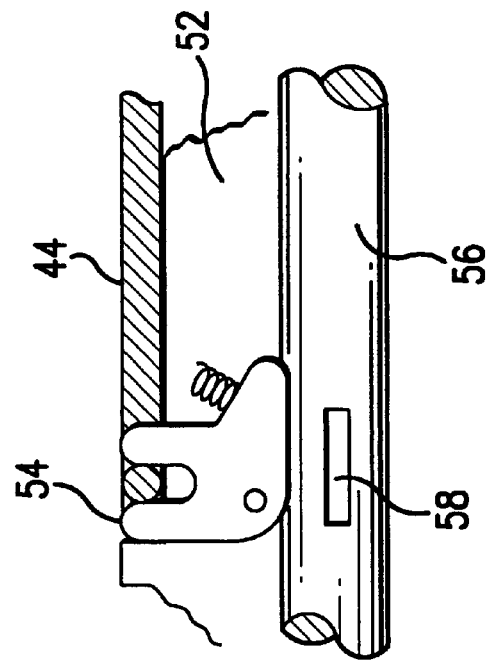
FIGS. 12A and 12B show the operation of the interlock mechanism for the cutting instrument for preparation of the implant site.
Figure 12A:
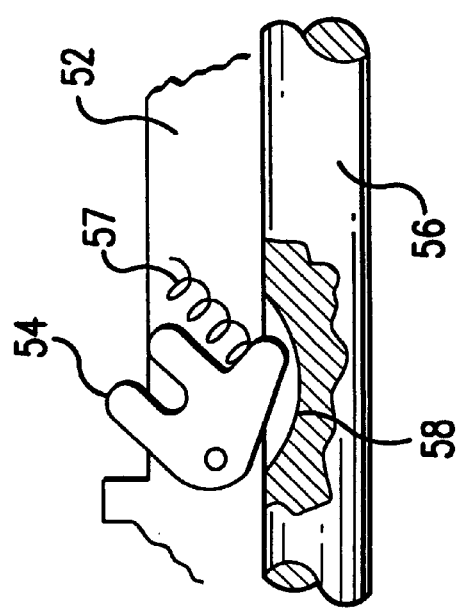

The end-cut tool 25, shown in FIGS. 11A and 11B, is inserted into the guide 44 to make an end-cut 52, shown in FIG. 11B, for the dovetail. Once completely inserted to the depth stop 53, a single piece interlock 54, shown in FIGS. 12A and 12B, which prevented rotation of the blade 55 during insertion, is disengaged from the shaft 56 and then prevents withdrawal of the end cut tool 52 from the guide 44. As shown in FIGS. 12A and 12B, the interlock 54 is held by spring 57 such that it engages the slot 58 in the shaft 56, preventing rotation as shown in FIG. 12A. As the end cut tool 52 is inserted into the guide 44 it pushes the interlock 54, rotating it out of the slot 58 in the shaft 56 as shown in FIG. 12B. As the interlock rotates, it engages the guide 44 as shown in FIG. 12B. When the shaft 56 is rotated as shown in FIG. 12B the interlock 54 cannot return to its original position as shown in FIG. 12A, thus securing the end cut tool 52 in the guide 44. The rotation interlock protects the surgeon from the end cut blade 55 and the withdrawal interlock holds the end cut tool 52 in the guide 44 while the blade 55 is exposed. The surgeon rotates the handle 59 one turn, causing the end cut blade 55 to make end-cuts 25 as shown in FIG. 11B, in both vertebrae 47 simultaneously, and returns it to the "zero" position at which the end cut tool 52 can be removed from the guide 44.

Figure 13A:
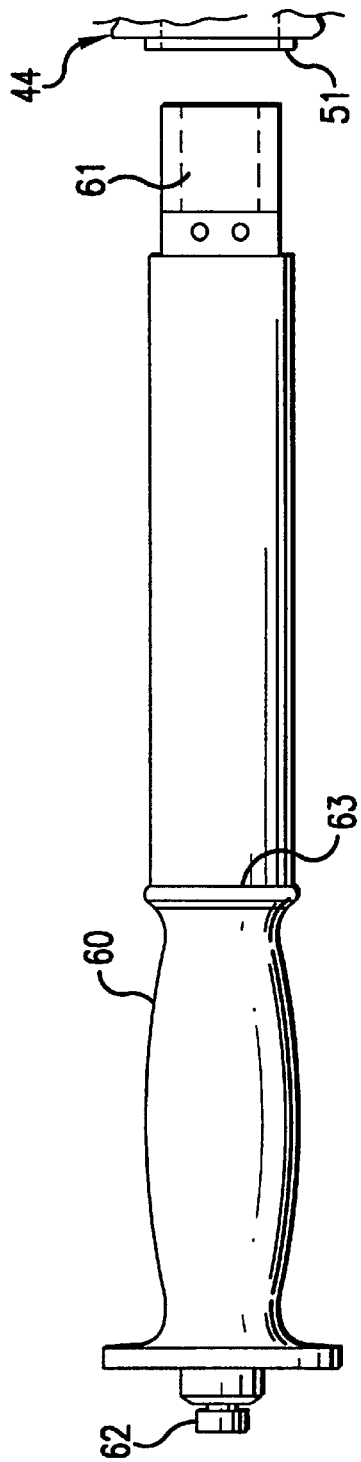
FIGS. 13A, 13B, and 13C show the cutting instrument for preparation of the implant site with dovetail tome deployed.
Figure 13C:
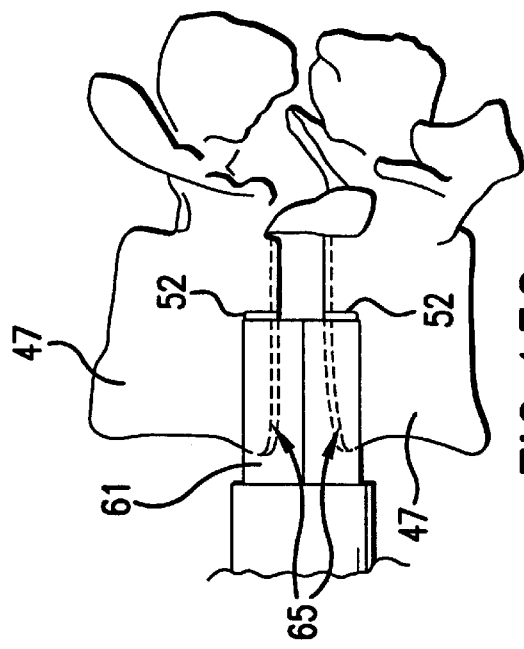
Figure 13B:
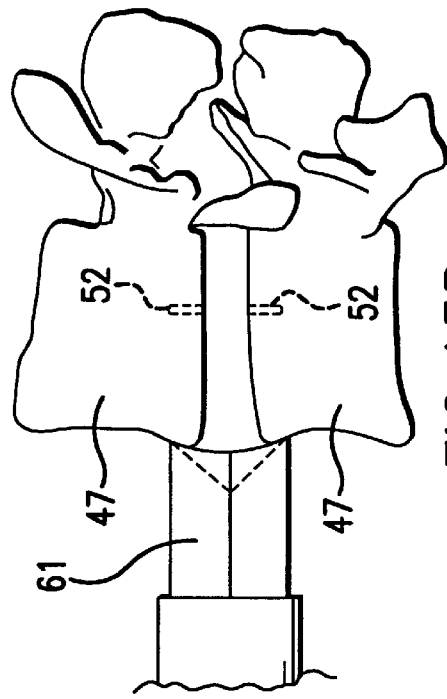
Figure 14B:
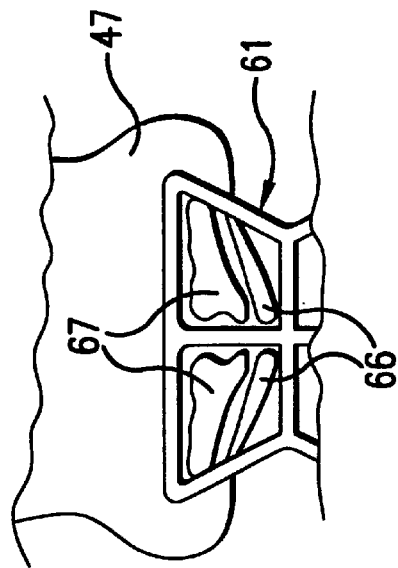
FIGS. 14A and 14B display details of the dovetail tome.
Figure 14A:
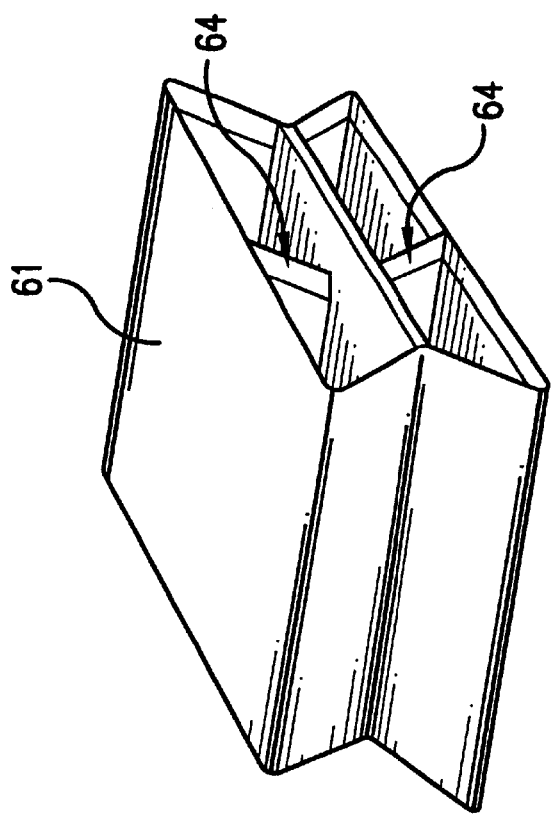
Figure 16A:
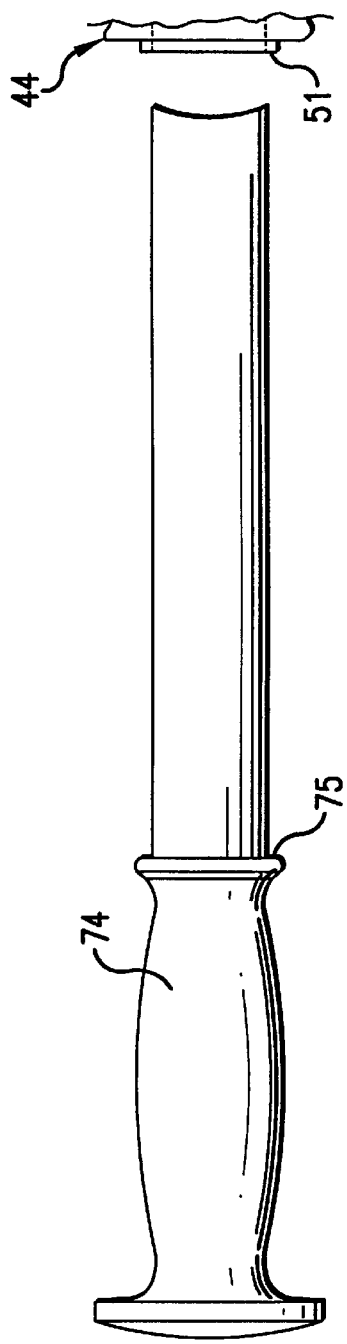
FIGS. 16A and 16B show detail of the placement implement.
Figure 16B:
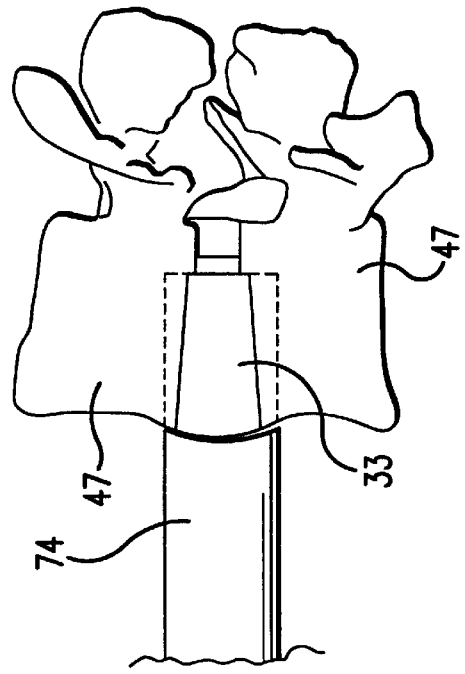

The dovetail tome 60, shown in FIG. 13A, is inserted into the guide 44 to the point where the blade 61 rests against the vertebrae 47. As shown in FIG. 15, the driver 68 is placed on the dovetail tome rod extension 62 and drives the dovetail tome 60, cutting the vertebrae 47, until the depth stop 63 of the dovetail tome contacts the stop 51 on the guide 44, stopping the blade 61 at the end-cut 52, as shown in FIG. 13C. The dovetail tome blade 61, as shown in FIG. 14A, has endplate breakers 64 which split the endplates 65 of the vertebrae (see FIG. 13C) in two 66 as shown in FIG. 14B, preventing them from jamming in the blade and preparing them for later use. The dovetail tome 60 is removed and the bone 67 and the split vertebral end plate 66 contained in the blade 61 is harvested for later use in the implant 33.

As shown in FIG. 15, the driver 68 is a pneumatic tool like a miniature jackhammer. The driver 68 is powered by compressed gas supplied through the input tube 69. The driver 68 receives the rod extension from the guide adapter 70 or the rod extension of dovetail tome 62 into a guide port 71. A piston 72, within the driver 68, repeatedly impacts the guide adapter 70 or the dovetail tome rod extension 62, driving the tool into place. The driver 68 is activated by the finger-actuated valve 73. Control of the force and rate of the impacts is attained by modulating the valve 73. The driver will deliver several thousand small impacts in place of a few massive blows from a hammer.

The implant 33 of FIG. 5 is prepared for insertion by filling the interior portion 34 with harvested bone 67 and the split end plates 66 from the dovetail tome cuts and additional bone and graft stock. The implant 33 is then slid down the guide 44 (FIG. 10) and driven into place by the insertion tool 74, shown in FIGS. 16A and 16B. The insertion tool 74 has a positive stop 75 which contacts the depth stop 51 of the guide 44 and assures correct placement of the implant 33, locking the vertebrae 47.

The above implant devices contain attachment means which are well known in the woodworking industry, but are not used in Orthopedic Spine Surgery. However, one skilled in the art of intervertebral implants would readily be able to adapt other fastening devices known in the woodworking art to spinal implant devices. It should be readily apparent to anyone skilled in the art that there are several available means to attach bone surfaces to the adjacent implant surfaces, such as causing bone anchors to protrude from the implant surface and impinge and attach the adjacent vertebrae to the implant. Metal staple-like clips can be driven between adjacent vertebrae to attach the edges of the vertebrae. Tack and staple configurations can substitute for the dovetail tongue and groove fasteners. Bone anchors can also be used to attach natural tissue to adjacent vertebrae, creating an artificial ligament which could scar down, thus retaining an artificial implant within the disc space while osteoinduction takes place and the vertebrae fuse.

We claim:

1. A tome for precisely cutting in two bone segments simultaneously in each of said segments a groove having the shape of an intimately mating dovetail, said tome comprising a shaft having first and second ends, said first end having attached thereto a blade shaped for cutting said dovetail grooves in said bone segments and said second end having attached thereto an extension for engagement with mechanical energy transmission devices, wherein the blade is configured to cut a first dovetail groove in a first vertebra and a second dovetail groove in a second vertebra simultaneously, said blade having a shape comprising a plurality of substantially planar segments connected by short radius curved segments.

2. The tome of claim 1 wherein said first and second vertebrae are each adjacent to a space left by surgically removed spinal tissue.

3. The tome of claim 1 additionally comprising an inclined blade which parts bone removed by the tome so as to prevent jamming of the tome.

4. The tome of claim 1 wherein the blade has endplate breakers for splitting endplates of the vertebrae in two thereby preventing them from jamming in the blade and preparing them for later use.

5. A tome for cutting a dovetail in each of two vertebrae, each of said vertebrae being adjacent to a space left by surgically removed spinal tissue, said tome comprising
   A) a substantially cylindrical shaft having first and second ends,
      i) said first end having attached thereto a blade for simultaneously cutting a dovetail in each of said vertebrae, said blade having endplate breakers for splitting endplates of the vertebrae in two thereby preventing them from jamming in the blade and preparing them for later use, and
      ii) said second end having attached thereto an extension for engagement with mechanical energy transmission means; and
   B) a depth stop on said shaft between said blade and said extension.

6. In combination with a tome for cutting at least one dovetail in bone comprising a shaft having first and second ends, said first end having attached thereto a blade for cutting said dovetail in said bone and said second end having attached thereto an extension for engagement with mechanical energy transmission means, a guide comprising a tube having a first end and a second end, said tube being configured for acceptance of said shaft of said tome and having tangs extending from one end thereof.

7. The combination of claim 6 wherein the bone is at least one vertebra.

8. The combination of claim 7 wherein the blade is configured to cut a first dovetail in a first vertebra and a second dovetail in a second vertebra.

9. The combination of claim 8 wherein said first and second vertebrae are each adjacent to a space left by surgically removed spinal tissue.

10. The combination of claim 9 wherein the tangs are adapted for insertion between the vertebrae to distract said vertebrae to a preferred dimension.

11. The combination of claim 10 wherein the tangs are tapered to conform to natural lordosis.

12. The combination of claim 10 further comprising a depth stop on said shaft between said blade and said extension.

13. The combination of claim 9 wherein the blade has endplate breakers for splitting endplates of the vertebrae in two thereby preventing them from jamming in the blade and preparing them for later use.

14. The combination of claim 6 wherein the shaft is substantially cylindrical.

15. The combination of claim 6 further comprising a depth stop on said shaft between said blade and said extension.

16. In combination with a tome for cutting a dovetail in each of two vertebrae, each of said vertebrae being adjacent to a space left by surgically removed spinal tissue, said tome comprising A) a substantially cylindrical shaft having first and second ends,
  i) said first end having attached thereto a blade for simultaneously cutting a dovetail in each of said vertebrae, said blade having endplate breakers for splitting endplates of the vertebrae in two thereby preventing them from jamming in the blade and preparing them for later use, and
  ii) said second end having attached thereto an extension for engagement with mechanical energy transmission means; and
B) a depth stop on said shaft between said blade and said extension, a guide comprising a tube having a first and second end, said tube being configured for acceptance of said shaft of said tome and having tangs tapered to conform to natural lordosis extending from one end thereof adapted for insertion between the vertebrae to distract said vertebrae to a preferred dimension.

17. The tome of claim 16 in which the at least one space comprising an element of an interlocking joint comprises a dovetail shape.

18. A tome for cutting in bone adjacent to excised tissue at least one space comprising an element of an interlocking joint, said tome comprising A) a shaft having first and second ends, said first end having attached thereto a blade shaped for cutting said space comprising an element of an interlocking joint in said bone and said second end having attached thereto an extension for engagement with mechanical energy transmission devices, said space comprising an element of an interlocking joint being configured to mate interlockingly with a complementary protrusion on an implant so as to form said interlocking joint, and said blade being configured to cut a space sufficiently accurately that the surface of the space and the surface of the implant mate intimately so as to promote bone ingrowth, and
a depth stop on said shaft between said blade and said extension.

19. A method for surgical fusion of vertebrae adjacent to a space left by excision of damaged spinal tissue comprising the steps of a. utilizing a tome shaped for cutting a space in said spinal tissue, said tome comprising
  i. a shaft having first and second ends, said first end having attached thereto a blade shaped to cut said space in each of said adjacent vertebrae and said second end having attached thereto an extension for engagement with mechanical energy transmission devices, and
  ii a depth stop on said shaft between said blade and said extension; and
b. inserting an implant configured to mate interlockingly with said space so as to mate the implant and said space interlockingly and with intimate surface contact so as to promote bone ingrowth.

20. A tome for cutting at least one dovetail groove in bone comprising

A) a shaft having first and second ends, said first end having attached thereto a blade shaped for cutting said dovetail in said bone and said second end having attached thereto an extension for engagement with mechanical energy transmission devices, and
B) a depth stop on said shaft between said blade and said extension.

21. A tome for cutting more than one dovetail in bone comprising a shaft having first and second ends, said first end having attached thereto a blade shaped for cutting said dovetails in said bone and said second end having attached thereto an extension for engagement with mechanical energy transmission devices; wherein the blade is configured to cut a first dovetail in a first vertebra and a second dovetail in a second vertebra simultaneously and has endplate breakers for splitting endplates of the vertebrae in two thereby preventing them from jamming in the blade and preparing them for later use.

* * * * *